United States Patent
DuBourdieu et al.

(10) Patent No.: US 9,662,356 B1
(45) Date of Patent: May 30, 2017

(54) PROPOLIS-METAL NANOPARTICLE COMPOSITION AND METHODS OF USE

(71) Applicant: Vets Plus, Inc., Knapp, WI (US)

(72) Inventors: Daniel J. DuBourdieu, Limerick, ME (US); Rajiv Lall, Menomonie, WI (US); Milind Deshpande, Coralville, IA (US)

(73) Assignee: VETS PLUS, INC., Knapp, WI (US)

( * ) Notice: Subject to any disclaimer, the term of this patent is extended or adjusted under 35 U.S.C. 154(b) by 0 days.

(21) Appl. No.: 15/011,935

(22) Filed: Feb. 1, 2016

Related U.S. Application Data

(60) Provisional application No. 62/110,820, filed on Feb. 2, 2015.

(51) Int. Cl.
| | |
|---|---|
| *A61K 35/644* | (2015.01) |
| *A61K 33/38* | (2006.01) |
| *A61K 31/12* | (2006.01) |
| *A61K 36/61* | (2006.01) |
| *A61K 47/10* | (2017.01) |
| *A61K 9/00* | (2006.01) |
| *A61K 9/06* | (2006.01) |
| *A61K 45/06* | (2006.01) |

(52) U.S. Cl.
CPC .......... *A61K 35/644* (2013.01); *A61K 9/0046* (2013.01); *A61K 9/06* (2013.01); *A61K 31/12* (2013.01); *A61K 33/38* (2013.01); *A61K 36/61* (2013.01); *A61K 45/06* (2013.01); *A61K 47/10* (2013.01)

(58) Field of Classification Search
None
See application file for complete search history.

(56) References Cited

U.S. PATENT DOCUMENTS 5,843,930 A * 12/1998 Purwar ............... A61K 9/0046
424/437
2010/0178255 A1* 7/2010 Kotha ................ A61K 9/0046
424/45

OTHER PUBLICATIONS

Lozina et al. ("Efficacy of Argentine propolis formulation for topical treatment of canine otitis externa", 2010).*
Roy et al. ("Biogenic synthesis of Au and Ag nanoparticles by Indian propolis and its constituents", 2010).*
Galdiero et al., Silver Nanoparticles as Potential Antiviral Agents. Molecules. 2011, 16, 8894-8918.
Kim et al., Antimicrobial effects of silver nanoparticles Nanomedicine: Nanotechnology, Biology, and Medicine 3 (2007) 95-101.
Kujumgiev et al., Antibacterial, antifungal and antiviral activity of propolis of different geographic origin. J Ethnopharmacol. Mar. 1999;64(3):235-40.
Kvitek et al., Antibacterial activity and toxicity of silver—nanosilver versus ionic silver. Journal of Physics: Conference Series 304 (2011).
Lozina et al., Eficacia del propóleos sobre Malassezia pachydermatis, correlación de distintas técnicas in vitro. Acta Farm. Bonaerense, v.25, p. 560-563, 2006.
Lozina et al., Efficacy of Argentine propolis formulation for topical treatment of canine otitis externa Arq. Bras. Med. Vet. Zootec., v.62, N. 6, p. 1359-1366, 2010.
Stebounova et al., Nanosilver induces minimal lung toxicity or inflammation in a subacute murine inhalation model. Part Fibre Toxicol. Jan. 25, 2011;8(1):5. doi: 10.1186/1743-8977-8-5.

* cited by examiner

*Primary Examiner* — Robert A Wax
*Assistant Examiner* — Quanglong Truong
(74) *Attorney, Agent, or Firm* — Charles S. Sara; DeWitt Ross & Stevens, S.C.

(57) ABSTRACT

A composition for the treatment of otitis in a mammal includes therapeutically anti-otitis effective amounts of propolis compounds in a pharmaceutically acceptable carrier, along with an antimicrobial metal-containing nanoparticles selected from the group consisting of silver, gold, aluminum, copper and zinc; and curcumin in a pharmaceutically acceptable carrier. In addition, the invention is directed to a method of treating an animal suspected of suffering from otitis comprising administering to an ear of the animal a composition as described above.

23 Claims, No Drawings

PROPOLIS-METAL NANOPARTICLE COMPOSITION AND METHODS OF USE

CROSS-REFERENCE TO RELATED APPLICATION

The application claims priority to U.S. Provisional Application entitled "PROPOLIS-METAL NANOPARTICLE COMPOSITION AND METHODS OF USE," Ser. No. 62/110,820 filed Feb. 2, 2015, which is incorporated herein by reference in its entirety.

BIBLIOGRAPHY

Complete bibliographical citations to the documents cited herein can be found in the Bibliography, immediately preceding the claims.

FIELD OF THE INVENTION

The invention relates to compositions containing propolis compounds and metal-containing nanoparticles for reducing infections and inflammation in the ear, such as the external ear canal, of animals.

BACKGROUND

Otitis externa is a condition characterized by inflammation of the external ear canal. The external ear canal is distal to the tympanic membrane. The ear pinna may or may not be involved in otitis externa.

Ear infections such as otitis externa represent one of the main reasons that dogs are presented to veterinarians, and may affect up to 20 percent of them. Dogs with otitis externa often present with swelling and erythema of the epithelial tissue of the ear canal, increased discharge from the ceruminous glands in the ear, and behavior suggesting pain and pruritus. Clinical signs can include any combination of headshaking, odor, pain on manipulation of the ear, exudate, and erythema. Otitis externa can occur in various mammals besides dogs, including cats and rabbits among others. Environmental factors such as high temperature and humidity can influence the incidence of otitis externa in dogs.

Some dog breeds, particularly those with large or hairy ears like cocker spaniels, miniature poodles or Old English sheepdogs, are more prone to ear infections, but they may occur in any breed. Many dogs will have more than one type of ear infection present (e.g., a bacterium and a fungus, or two kinds of bacteria). Many dogs with chronic or recurrent ear infections have allergies or low thyroid function (hypothyroidism).

The external ear canals of most dogs and cats harbor small numbers of commensal gram-positive cocci. Gram-negative bacteria are also present. These organisms may become pathogenic if the microenvironment is changed and encourages their overgrowth. Aside from bacteria, other primary causes of otitis externa include allergy, autoimmune (e.g., pemphigus), endocrine dysfunction, epithelialization disorders, foreign bodies, glandular disorders, immune-mediated (e.g., drug reactions), fungal (e.g., aspergillosis), parasites, viral (e.g., canine distemper), and miscellaneous (auricular chondritis, eosinophilic diseases, juvenile cellulitis, proliferating necrotizing otitis of cats).

Infectious bacteria in otitis externa can include *Staphylococcus aureus* or *Pseudomonas aeruginosa* but in many cases there are numerous types of bacteria observed. Coccal organisms are usually staphylococci or streptococci. Rod-shaped organisms are usually *Pseudomonas aeruginosa, Escherichia coli, Proteus vulgaris*, or *Proteus mirabilis*. The presence of many neutrophils confirms the pathogenic nature of the organisms. Methicillin-resistant *Staphylococcus intermedius* and *Pseudomonas* otitis (caused by *Pseudomonas aeruginosa*) have emerged as frustrating and difficult perpetuating causes of otitis because of the development of resistance to most common antibiotics. These infections are often chronic in course (>2 month) and associated with marked suppurative exudation, severe epithelial ulceration, pain, and edema of the canal.

Infectious yeasts that cause otitis externa include *Malassezia pachydermatis, Aspergillus niger*, and *Candida albicans*, among others. *M. pachydermatis* is found in low numbers in the ear canals of many healthy dogs and cats. Because yeasts colonize the surface of the ear canal, they are most easily found adhered to clumps of exfoliated squamous epithelial cells. *M. pachydermatis* is identified readily on microscopic examination and its numbers easily assessed. There is no specific number that indicates yeast overgrowth. The key determining factor is whether the ears are pruritic.

Otitis externa can also be caused by viral infections that can be from herpes simplex and herpes zoster infections, among others.

Agents, compositions, and methods of treating otitis externa are needed especially caused by antibiotic resistant strains bacteria.

SUMMARY OF THE INVENTION

The present invention is directed to a composition comprising metal-containing nanoparticles, propolis compounds, curcumin, and essential oils for the treatment of otitis or otitis externa. The composition is effective against both gram-negative and gram-positive bacteria, which are causative microbes to be controlled in animals with otitis externa.

Specifically, the present invention is directed to a composition for the treatment of otitis in a mammal comprising therapeutically anti-otitis effective amounts of propolis compounds in a pharmaceutically acceptable carrier.

The invention is further directed to a composition for the treatment of otitis in a mammal comprising therapeutically anti-otitis effective amounts of propolis compounds; an antimicrobial metal-containing nanoparticle selected from the group consisting of silver, gold, aluminum, copper and zinc; and curcumin in a pharmaceutically acceptable carrier.

Still further, the present invention is directed to a method of treating an animal suspected of suffering from otitis comprising administering to an ear of the animal a composition comprising therapeutically anti-otitis effective amounts of propolis compounds in a pharmaceutically acceptable carrier.

The invention is also directed to a method of treating an animal suspected of suffering from otitis comprising administering to an ear of the animal a composition comprising therapeutically anti-otitis effective amounts of propolis compounds; an antimicrobial metal-containing nanoparticle selected from the group consisting of silver, gold, aluminum, copper and zinc; curcumin; essential oils, selected from the group consisting of clove oil, garlic oil, lavender oil, tea tree oil, ginger oil and sesame oil; and a corticosteroid in a pharmaceutically acceptable carrier.

The objects and advantages of the invention will appear more fully from the following detailed description of the preferred embodiment of the invention.

DETAILED DESCRIPTION OF THE INVENTION

Propolis:

Components in the composition of the invention include propolis compounds. The propolis compounds can be provided in any number of forms, including crude propolis or propolis extracts.

Propolis is a wax-cum-resin substance that is produced by bees. Propolis is made from substances collected by bees from tree buds which are then digested and mixed with the substance secreted by bee's glands. Over 300 chemical compounds are described in various propolis origins. The chemicals constituents include waxes, resins, balsams, oils and ether, pollen and organic material. The proportion of these substances varies and depends on the place and period of collection.

The collected propolis from a bee hive, also known as crude propolis, typically contains about 50% plant resins, 30% beeswax, 10% essential oils, 5% pollen, and 5% debris of wood and earth. Propolis also contains various organic acids, a considerable amount of minerals (including, manganese, zinc, calcium, phosphorous, copper), vitamins B1, B2, B6, C and E, acids (nicotinic acid and pantothenic acid) and amino acids. The composition of chemical compounds is responsible for the properties of propolis.

Propolis compounds have anti-inflammatory effects, immunostimulator activity, and antimicrobial activity against a number of microorganisms. The antimicrobial activity includes antibacterial activity, antifungal activity, and antiviral activity. Propolis compounds have antimicrobial activity against, e.g., *Staphylococcus aureus* and *Escherichia coli*, among others, and antifungal activity against, e.g., *Candida albicans* and others. Gram-positive bacteria are more susceptible to propolis compounds than Gram-negative bacteria. The antibacterial activity results at least in part by the presence of flavonoids, aromatic acids and esters, cinnamic acid, and coumarin. The antiviral activity appears to result at least in part from the presence of flavonoids, aromatic acids, and derivatives thereof. The chemical content of propolis depends on the geographic zone from which it is obtained. However, the anti-inflammatory, immunostimulator, and antimicrobial activities of propolis are independent of its origin. Therefore, propolis compounds obtained from any propolis source can be used in the present invention.

The propolis compounds that may be included in the compositions of the present invention preferably include the compounds that are present in ethanol extracts of propolis. Thus, at least in some versions of the invention, "propolis compounds" refers to the compounds obtained from ethanol extraction of propolis, or chemically modified derivatives thereof, regardless of the propolis source. Such propolis compounds may be provided in the form of crude propolis, the ethanol extracts themselves, processed ethanol extracts, chemically modified ethanol extracts, or compositions comprising manually combined isolated or synthesized compounds that together constitute the constituent compounds present in ethanol extracts of propolis. An exemplary method of ethanol extraction of propolis includes combining the propolis with ethanol (e.g., 95% ethanol) for a defined period of time (such as 24 hours), followed by filtering the ethanol suspension. The ethanol may be removed by evaporation or other means to result in a powder. Other methods of performing ethanol extraction of propolis are acceptable. In some versions of the invention, "propolis compounds" refers to the compounds, or chemically modified derivatives thereof, obtained from extraction of propolis with water, glycol or oil (such as olive oil), regardless of propolis source.

The propolis compounds may be included in the composition in an amount of from about 0.0001% w/w to about 80% w/w, preferably from about 0.1% to about 50% and more preferably from about 0.5% to about 15%. The propolis compounds are preferably present in the composition in an amount sufficient to confer an anti-otitis or anti-otitis externa effect. Such effects may include any one or more of an antimicrobial effect, an antibacterial effect, an antifungal effect, an antiviral effect, an anti-inflammatory effect, and an immunostimulator effect.

Metal-Containing Nanoparticles:

Components in the composition of the present invention may also contain metal-containing nanoparticles. The metal-containing nanoparticles may consist entirely of metal or may comprise metal in addition to other components, such as polymers (as used in polymer coatings, etc.) or other components. Each individual metal-containing nanoparticle may consist of only one type of metal or may comprise a plurality of types of metals. Furthermore, the group of metal-containing nanoparticles may consist of particles substantially identical in composition or may comprise particles having different compositions, such as a sub-group of particles comprised of one metal and a sub-group of particles comprised of another metal. The metal in the metal-containing nanoparticles may include any one or more of silver, gold, aluminum, copper, and zinc, among other metals having antimicrobial properties when formulated as nano-sized particles. Inclusion of at least silver is preferred but not required. The metal-containing nanoparticles are preferably in a form capable of releasing ions of the metal, such as through oxidation of the metal.

In some versions of the invention, the average size of the metal-containing nanoparticles in the composition may range from about 0.1 nm to about 200 nm, such as from about 0.1 nm to about 100 nm or from about 0.1 nm to about 15 nm.

The metal-containing nanoparticles may be present in the composition in an amount of from about 1 ppb to about 100,000 ppm, more preferably about 0.1 ppm to about 50,000 ppm, more preferably still about 0.1 ppm to about 100 ppm, and most preferably about 1 to about 50 ppm.

The metal-containing nanoparticles are preferably present in the composition in an amount sufficient to confer an anti-otitis or anti-otitis externa effect. Such effects may include any one or more of an antimicrobial effect, an antibacterial effect, an antifungal effect, and an antiviral effect.

Silver Nanoparticles:

Components in the composition of the invention may also include silver salts or nanoparticles of silver. The preferred metal particles are nano-sized particles of elementary silver, silver ions or silver salts. Due to their small size, these nanoparticles are able to invade bacteria and other microorganisms and kill them. The term "silver nanoparticles" or "nanosilver" of the invention refers to particles made from elemental silver, silver ions or silver salts. However, the silver salts of the invention can also be found at a different scale sizes. The silver salts can exist as powders that can also be solubilized by water and exist as highly reactive individual silver ions. These silver ions are on the scale of an individual atom size, which is much smaller scale than the nanoscale.

Silver nanoparticles, otherwise known as nanosilver or nanosilver particles, are preferred metal-containing nanoparticles. Silver nanoparticles are highly toxic to microorganisms, including bacteria, yeast, and viruses. Silver nanoparticles appear to be more effective against Gram-negative bacteria, such as *E. coli*, than Gram-positive bacteria, such as *Staphylococcus aureus*. Silver nanoparticles can kill bacteria and viruses at concentrations that are not toxic to mammalian cells.

The antibacterial effects of silver salts have been known since antiquity, and silver is currently used to control bacterial growth in a variety of applications, including dental work, catheters, and burn wounds. In fact, it is well known that silver ions and silver-based compounds are highly toxic to microorganisms, showing strong biocidal effects on as many as twelve species of bacteria including *E. coli*. The medicament is administered in a dose comprising about of 1 to 2 mg of silver ions or silver salts per Kg of composition of the present invention.

While the antimicrobial effects of silver (Ag) ion or salts are well known, the effects of silver nanoparticles on microorganisms and antimicrobial mechanism are not fully understood. There appears to be variable results in the use of nanosilver particles for its efficacy against pathogenic microbes. For example, it was shown that yeast and *E. coli* were inhibited at the low concentration of silver nanoparticles, whereas the growth-inhibitory effects on *Staphylococcus aureus* were mild (Kim).

Silver nanoparticles have mainly been studied for their antimicrobial potential against bacteria, but have also proven to be active against several types of viruses including human immunodeficiency virus, hepatitis B virus, herpes simplex virus, respiratory syncytial virus, and monkey pox virus. The use of metal nanoparticles provides an interesting opportunity for novel antiviral therapies especially in otitis applications for companion animals. Since metals may attack a broad range of targets in the virus (Galdiero) there is a lower possibility to develop resistance as compared to conventional antivirals.

Curcumin:

The invention may also contain curcumin in conjunction with the other antimicrobial actives, as an anti-inflammatory agent. The curcumin is selected from natural derivatives of curcuminoids found in yellow turmeric and white turmeric, including curcumin, desmethoxycurcumin, bis-desmethoxycurcumin, tautomeric forms including 1,3-diketo forms and enol forms along with tetra hydro curcumins and in nano-sized particles. This yellow pigmented polyphenol has been studied extensively in human clinical research as a natural agent to fight inflammatory conditions. The turmeric may be extracted to obtain the curcumin. The curcumin or curcumin extract is present in an amount of from about 0.001% w/w to 5% w/w, and preferably in an amount of about 0.5% to 5% w/w in the invention.

Essential Oils:

Certain essential oils have been used to help reduce problems associated with ear aches and otitis externa. The invention may contain essential oils in conjunction with the other antimicrobial agents. One such oil is from clove. Clove oil has been used as a topical anesthetic and as antimicrobial agent for many years. It also smells pleasant to most people. One of the characteristics of canine otitis externa is a foul odor and a pleasant smell during application of the invention is an improvement over other treatment currently used. The use of clove oil in the invention can provide a pleasant smell to the invention itself while also providing additional antimicrobial and pain killing aspects that are associated with the problem. The concentration of oil is from 0.001% w/w to 10% w/w and preferably from 0.1 to 2% w/w and more preferably from 0.5 to 1.5% w/w. Other oils that are known to have antimicrobial activity that can be used in the invention include garlic oil, lavender oil, tea tree oil, ginger oil, and sesame oil.

Corticosteroid:

In some versions, the composition further comprises a corticosteroid. Preferred corticosteroids are glucocorticoids. Suitable glucocorticoids include but are not limited to cortisol (hydrocortisone), cortisone, prednisone, prednisolone, methylprednisolone, dexamethasone, betamethasone, triamcinolone, beclometasone, fludrocortisone acetate, deoxycorticosterone acetate, and aldosterone. The corticosteroid is preferably included in the composition in an amount sufficient to elicit an anti-otitis or anti-otitis externa effect. The concentration of corticosteroid is from 0.001% w/w to 1% w/w and preferably from 0.005 to 1% w/w and more preferably from 0.025 to 0.1% w/w.

In some versions, the composition further comprises pain medications, such as tramadol and/or others; antibiotics; and/or anti-inflammatory agents other than those explicitly described herein.

Forms:

The composition of the invention can be in various forms, such as a liquid or semi-solid form. Various specific forms include but not limited to solution, spray, gel, ointment, or emulsion in the form of liquid suspension, lotion, or cream. The composition can also be integrated into an absorbent material, such as a wick of cotton fabric or medical dressing, which can be placed into the external auditory canal. Furthermore, the composition can also be in the form of lipid or polymeric vesicles or polymeric patches or hydrogels for controlled release. Pharmaceutically acceptable carriers or media suitable for topical application into the external auditory canal and the auricle are known to those skilled in the art.

The solutions and suspensions may be formulated with solvents such as water, glycerol, diluted alcohol, and/or propylene glycol, among others.

In some embodiments, the composition comprises one or more surfactants that enhance wetting of the external auditory canal and facilitate spreading of the composition on the epithelial lining of the external auditory canal. It is known that the cerumen exudate, normally secreted upon the epithelial tissue lining the external auditory canal, is a waxy material that imparts a high surface tension thereto which is useful in preventing foreign matter from reaching the tympanic membrane and effecting the middle and inner ear. During otitis externa, cerumen production increases in response to inflammation of the epithelial lining of the external auditory canal. Moreover, during otitis externa, proteinaceous inflammatory waste materials resulting from the lysis, phagocytosis and necrosis of antigenic material secrete in the external auditory canal. These secreted substances form a coating upon the epithelial lining of the external auditory canal and tend to inhibit uniform or effective application of aqueous ear drops on the epithelial lining of the external auditory canal in the treatment of the inflammatory condition.

Surfactants are usually organic compounds that are amphiphilic, containing both hydrophobic tail groups and hydrophilic head groups. Surfactants reduce the surface tension of water by adsorbing at the liquid-gas interface, and reduce the interfacial tension between oil and water by adsorbing at the liquid-liquid interface. The surfactant that may be included in the composition functions as a wetting agent, which reduces surface tension of the external auditory canal. A composition containing suitable surfactants spreads more uniformly on the surface of the external auditory canal. Moreover, surfactant molecules form vesicles and/or micelles, which facilitate penetration and delivery of the effective agents in the composition through the secreted substances into the tissue. Various commercial available surfactants can be used in the composition. The surfactants can be anionic, cationic, non-ionic, zwitterionic surfactants, or combinations thereof.

In some versions, the composition is in the form of a lotion. The lotion preferably has a substantially neutral pH, i.e., from about 6 to about 7. The lotion may contain any one or more of purified water, glycerin, hydrogenated polyisobutene, cetearyl alcohol and ceteareth-20, macadamia nut oil, dimethicone, tocopheryl acetate, stearoxytrimethylsilane and stearyl alcohol, panthenol, farnesol, benzyl alcohol, phenoxyethanol, acrylates/C 10-30 alkyl acrylate crosspolymer, sodium hydroxide, and citric acid, among other ingredients. A commercially available moisturizing lotion manufactured by Galderma Laboratories, Inc. (Lausanne, Switzerland) under the trademark CETAPHIL moisturizing lotion may be used as the carrier for the metal-containing nanoparticles and/or propolis compounds of the composition of the invention.

In some versions, the composition is an emulsion. The emulsion may contain metal-containing nanoparticles and/or propolis compounds, one or more solvents, an oily phase, one or more surfactants as emulsifier, and water. The method of preparing an emulsion is known to those skilled in the art. The emulsion can be formulated into a solution, lotion, or cream. The emulsion can also be sprayable.

In some versions, the composition is an ointment. The ointments can be prepared using either an oleaginous base or medium or an absorbent base. The oleaginous base comprises fixed oils or hydrocarbons, such as white petrolatum, mineral oil (liquid paraffin), wool fat, yellow soft paraffin, olive oil, coconut oil. Olive oil, coconut oil, liquid paraffin, and other carriers are useful as ceruminolytic agents. The absorbent base comprises an anhydrous substance or substances which can absorb water, for example anhydrous lanolin. Following formation of the base, the nanoparticles and/or propolis compounds are added to an amount affording the desired concentration to form the composition. Ointments are very useful in managing dry scaly skin conditions of external auditory canal.

In some versions, the composition is a hydrogel, such as a thermal response hydrogel. Upon applying to the external auditory canal, the composition can change from a liquid suspension to gel and forms a coating within the auditory canal. The adhesion to the surface can facilitate delivery of the active component across the epithelial lining.

A non-limiting, exemplary composition of the invention can be prepared as follows. Propolis is sourced from appropriate geographical regions around the world and tested by in vitro assays for efficacy against microbial pathogens that cause otitis externa. Selected lots of propolis are then extracted with ethanol, and the ethanol extracts are dried to powder. The dried ethanol extracts are then mixed into a suitable carrier at a concentration ranging from 0.001% w/w to 80% w/w. Metal-containing nanoparticles and other antimicrobial agents are then mixed into the carrier. The carrier can include water, glycerol, diluted alcohol, propylene glycol liquid paraffin, lanolin, wool fat, and/or yellow soft paraffin, among other ingredients.

Methods of the invention include treating an animal suspected of suffering from otitis, suspected of suffering from otitis externa, suffering from otitis, or suffering from otitis externa by administering a composition as described herein to an ear of the animal. "Animal suspected of suffering from otitis" or "animal suspected of suffering from otitis externa" refers to any animal exhibiting symptoms associated with otitis or otitis externa, respectively, as described herein or otherwise known in the art. "Animal suffering from otitis" or "animal suffering from otitis externa" refers to any animal suffering from a diagnosable condition of otitis or otitis externa, whether actually diagnosed or not.

Any animal may be treated with the methods herein. Exemplary animals include mammals. Canids (includes dogs), felids (includes cats), caprines (includes goats, sheep, etc.), and leporids (includes rabbits and hares) are exemplary mammals.

The composition is preferably applied topically into the external auditory canal and on the auricle of the affected ear. The composition in the form of a lotion, gel, or ointment can be applied with an applicator. Preferably, the applicator has a smooth surface, for example, a glass rod coated with the lotion, gel, or ointment. A cotton swab can also be used. The composition in the form of liquid suspension can be dropped or sprayed into the external auditory canal. Moreover, the composition can also be integrated into or applied on an absorbent material, such as a strip of cotton fabric or medical dressing, and then the absorbent material is inserted into the external auditory canal. After administration, the ear can then be massaged to ensure distribution of the composition within the ear canal.

The composition can be applied to the affected ear one or more times a day, typically one to two times a day. When the pain is severe, the composition can be applied more frequently to help alleviate the symptoms.

In some embodiments, a suitable volume of administration ranges from about 0.1 ml to about 5 ml of the composition. Exemplary animals for treatment include dogs. The volume of the ear canal in most dogs is about 1 ml. An adequate treatment may comprise instillation of at least this volume once or twice daily.

The following examples are exemplary only and are not intended to limit the invention.

EXAMPLES

Example 1

Propolis was ground to a fine powder and extracted with 80% ethanol by maceration and agitation under dark and at room temperature. After three days, it was frozen overnight to −20° C., and then the mixture was centrifuged to obtain the supernatant, which was filtered through filter paper. This supernatant was dried by evaporation under vacuum at 40° C., and the crude propolis ethanolic extract (PEE) was stored in dark at 4° C. until mixing into a gel matrix. Ear drops in a topical gel matrix were prepared using 2.5% PEE in a mixture of glycerin-propylene glycol (1:1). Silver nanoparticles of 15-nm particle size were mixed into the matrix at a concentration of about 10 ppm. The composition was packaged in a dark glass eyedropper bottle and kept at room temperature (25±5° C.) until use.

Example 2

Exudates from a dog with otitis externa were collected. The exudates were cultured on agar plates to isolate bacteria that caused the otitis. Identified bacteria included *Rothia* species, *Bacillus* species, coagulase negative *Staphylococcus* group, *Staphylococcus intermedius* and *Enterococcus*

*gallinarum*. Isolated bacteria were grown on separate plates and holes were punched in the agar. Propolis extract was prepared by adding 160 grams of raw propolis into one liter of 80% ethanol. The mixture was heated to 80° C. for 30 minutes and then cooled. The liquid was centrifuged to remove any solids and the clarified liquid extract was used in the agar plates. Different concentrations of propolis extract were then placed in the holes. The agar plates were incubated, and clear zones of inhibition were observed in the agar plate due to the propolis. This indicates that the propolis extract effectively killed the bacteria that caused otitis externa in the dog in a dose dependent manner.

Example 3

The composition from Example 1 was placed on a shaved patch of normal dog skin on the back of a dog for 4 hours. The site was covered with gauze. Untreated skin areas served as the control. The gel matrix was removed and the skin was examined for any signs of inflammation. It was found that the composition caused no irritation or inflammation after 4 hours of contact time.

Example 4

A three year old German shepherd dog was presented with a history of inappetance, aural pruritus, head shaking and development of an odor in the ear. Physical examination revealed normal temperature, pulse and respiration rate. External ear examination revealed thickening of pinnae, erythema, scaling and presence of cerumen with yellow crusts consistent with symptoms of otitis externa. The affected ear was cleaned with physiological saline. The propolis extract prepared from example 2 was combined with an ethanol extract of curcumin. The ethanol extract of curcumin had been prepared by adding 16 g of turmeric to 100 mL of 80% ethanol and heating at 70° C. for 20 min. The ingredients of the invention were combined as found in table 2 and were applied locally @ 1 ml twice daily for 2 weeks. The ears were evaluated for skin erythema, edema, pain, pruritus and quantity of ceruminous exudate on day 0 and at day 14. These parameters are scored on a severity scale of 0-3 (0=none, 1=slight, 2=moderate, and 3=severe). Table 2 shows the results. The results indicated by day 14 total reduction of pain and pruritus while skin erythema, edema, and quantity of cerumen were dramatically reduced. These results indicate that the invention was very effective in reducing otitis externa in the dog within 2 weeks to near normal health conditions.

TABLE 1

| Ingredient | Amount |
| --- | --- |
| Glycerol | 50 mL |
| Propylene Glycol | 45 mL |
| Propolis Extract | 5 mL |
| Clove oil | 1 mL |
| Curcumin Extract | 1 mL |
| Polysorbate 80 | 0.2 g |

TABLE 2

Comparison of clinical parameters on day 0 and day 14

| Clinical parameters | Day 0 | Day 14 |
| --- | --- | --- |
| Skin erythema | 3 | 1 |
| Edema | 3 | 1 |
| Pain | 2 | 0 |
| Pruritus | 3 | 0 |
| Quantity of cerumen | 3 | 1 |
| Scales | 3 | 0 |

Example 5

A dog that had been suffering otitis externa for about a year was presented for use with the invention. The dog was exhibiting characteristic pruritus, inflammation, exudate and foul odor in the ear. The animal had been treated previously over the course of the year with numerous antibiotics including nystatin, neomycin, polymyxin B, but to no avail, thus indicating the presence of antibiotic resistant bacteria were causing the otitis externa. Various causative bacteria that were resistant to the antibiotic regimen were isolated from the ear exudate and identified to include *Rothia* species, *Bacillus* species, coagulase negative *Staphylococcus* group, *Pseudomonas aeruginosa, Staphylococcus intermedius* and *Enterococcus gallinarum*. The invention in table 1 was applied locally @ 1 ml twice daily for 2 weeks. After two weeks of treatment with the invention, the smell of otitis was gone, the exudate eliminated, the inflammation had been reduced back to normal conditions and the animal was not exhibiting signs of pruritus. The ear canal was swabbed to culture previously identified causative bacteria. None were found present in the ear. These results indicate that the invention can be used effectively on dogs that had previously been resistant to standard antibiotic treatments for otitis externa.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

Galdiero S. Annarita Falanga, Mariateresa Vitiello, Marco Cantisani. Silver Nanoparticles as Potential Antiviral Agents. Molecules. 2011, 16, 8894-8918.
Kujumgiev A, Tsvetkova I, Serkedjieva Y, Bankova V, Christov R, Popov S. Antibacterial, antifungal and antiviral activity of propolis of different geographic origin. J Ethnopharmacol. 1999 March; 64(3):235-40.
Kvitek L., A Panacek, R Prucek, J Soukupoval, M Vanickoval, M Kolar and R Zboril. Antibacterial activity and toxicity of silver-nanosilver versus ionic silver. Journal of Physics: Conference Series 304 (2011).
Kim Jun Sung, Eunye Kuk, Kyeong, Nam Yu, Jong-Ho Kim, et al. Antimicrobial effects of silver nanoparticles Nanomedicine: Nanotechnology, Biology, and Medicine 3 (2007) 95-101.
Lozina L A, Boehringer S, Oehringer S. Daquino M et al. Eficacia del propóleos sobre *Malassezia pachydermatis*, correlación de distintas técnicas in vitro. Acta Farm. Bonaerense, v. 25, p. 560-563, 2006.
Lozina, L. A., M. E. Peichoto, S. I. Boehringer, P. Koscinczuk, G. E. Granero, O. C. Acosta. Efficacy of Argentine propolis formulation for topical treatment of canine otitis externa Arq. Bras. Med. Vet. Zootec., v. 62, n. 6, p. 1359-1366, 2010.
Stebounova L V, Adamcakova-Dodd A, Kim J S, Park H, O'Shaughnessy P T, Grassian V H, Thorne P S. Nanosilver induces minimal lung toxicity or inflammation in a subacute murine inhalation model. Part Fibre Toxicol. 2011 Jan. 25; 8(1):5. doi: 10.1186/1743-8977-8-5.

What is claimed is:

1. A composition for the treatment of otitis externa in a mammal comprising therapeutically anti-otitis effective amounts of propolis and curcumin compounds, an antimicrobial metal-containing nanoparticle selected from the group consisting of silver, gold, aluminum, copper and zinc, and essential oils selected from the group consisting of clove oil, garlic oil, lavender oil, tea tree oil, ginger oil and sesame oil, in a pharmaceutically acceptable carrier.

2. The composition of claim 1 wherein the propolis compounds are provided as crude propolis.

3. The composition of claim 1 claim wherein the propolis compounds are provided as a propolis extract.

4. The composition of claim 1 wherein the propolis compounds are present in an amount of from about 0.0001% w/w to about 80% w/w.

5. The composition claim 1 wherein the metal-containing nanoparticles are present in an amount from about 1 ppb to about 100,000 ppm.

6. The composition of claim 1 wherein the metal-containing nanoparticles range in size from about 0.1 nm to about 200 nm.

7. The composition of claim 1 wherein the metal-containing nanoparticles range in size from about 0.1 nm to about 15 nm.

8. The composition of claim 1 wherein the metal-containing nanoparticles are present in an amount of from about 0.1 mg to about 100,000 mg per Kg of total composition.

9. The composition of claim 1 wherein the metal-containing nanoparticles are silver nanoparticles of elemental silver, silver ions or silver salts administered in an amount of from about 1 mg to 2 mg per Kg of total composition.

10. The composition of claim 1 wherein the curcumin is administered in an amount of from about 0.001% w/w to 5% w/w.

11. The composition of claim 1 wherein the essential oils are administered in an amount of from 0.001% w/w to 10% w/w.

12. The composition of claim 1 further comprising a therapeutically effective amount of a corticosteroid.

13. The composition of claim 12 wherein the corticosteroid is present in an amount of from 0.025% w/w to 0.1% w/w.

14. The composition of claim 12 wherein the corticosteroid is a glucocorticoid.

15. The composition of claim 1 wherein the composition is in a liquid or semi-solid form.

16. The composition of claim 1 wherein the pharmaceutically-acceptable carrier is selected from the group consisting of water, glycerol, diluted alcohol, propylene glycol liquid paraffin, lanolin, wool fat, yellow soft paraffin, and combinations thereof.

17. A method of treating an animal suspected of suffering from otitis externa comprising administering to an ear of the animal a composition comprising therapeutically anti-otitis effective amounts of propolis and curcumin compounds, and a therapeutically effective amount of an antimicrobial metal-containing nanoparticle selected from the group consisting of silver, gold, aluminum, copper and zinc, in a pharmaceutically acceptable carrier.

18. The method of claim 17 wherein the propolis compounds are present in an amount of from about 0.0001% w/w to about 80% w/w.

19. The method of claim 17 wherein the metal-containing nanoparticles are present in an amount from about 1 ppb to about 100,000 ppm.

20. The method of claim 17 wherein the metal-containing nanoparticles are silver nanoparticles of elemental silver, silver ions or silver salts administered in an amount of from about 1 mg to 2 mg per Kg of total composition.

21. The method of claim 17 wherein the composition further comprises a therapeutically effective amount of essential oils, selected from the group consisting of clove oil, garlic oil, lavender oil, tea tree oil, ginger oil and sesame oil, wherein the essential oils are administered in an amount of from 0.001% w/w to 10% w/w.

22. The method of claim 17 wherein the composition further comprises a therapeutically effective amount of a corticosteroid.

23. The method of claim 17 wherein the composition is in a liquid or semi-solid form.

* * * * *